United States Patent [19]

Kilpper et al.

[11] 4,328,339
[45] May 4, 1982

[54] CONTINUOUS PREPARATION OF ISATOIC ANHYDRIDE

[75] Inventors: Gerhard Kilpper, Battenberg; Johannes Grimmer, Ludwigshafen; Peter Tonne, Neustadt; Hans C. Horn, Lambsheim; Eckhard Hetzel, Bobenheim-Poxhe, all of Fed. Rep. of Germany

[73] Assignee: BASF Aktiengesellschaft, Fed. Rep. of Germany

[21] Appl. No.: 209,960

[22] Filed: Nov. 24, 1980

Related U.S. Application Data

[63] Continuation of Ser. No. 108,580, Dec. 31, 1979, abandoned.

[30] Foreign Application Priority Data

Jan. 26, 1979 [DE] Fed. Rep. of Germany ....... 2902978

[51] Int. Cl.$^3$ .......................................... C07D 265/26
[52] U.S. Cl. ..................................................... 544/94
[58] Field of Search .......................................... 544/94

[56] References Cited

U.S. PATENT DOCUMENTS

| 3,324,119 | 6/1967 | Hill et al. | 544/94 |
| 3,687,951 | 8/1972 | Humburger et al. | 544/95 |
| 3,847,974 | 11/1974 | Sturm et al. | 544/94 X |
| 3,984,406 | 10/1976 | Quadbeck-Seeger et al. | 544/94 |

FOREIGN PATENT DOCUMENTS

| 127138 | 3/1901 | Fed. Rep. of Germany | 544/94 |
| 1770458 | 10/1971 | Fed. Rep. of Germany | 544/94 |
| 2000698 | 7/1974 | Fed. Rep. of Germany | 544/94 |

OTHER PUBLICATIONS

Mohr, J. fur Prakt. Chemie (2), vol. 80, pp. 1–33, (1909).

*Primary Examiner*—Richard Raymond
*Attorney, Agent, or Firm*—Keil & Witherspoon

[57] ABSTRACT

A process for the continuous preparation of isatoic anhydrides by two-stage reaction of an alkali metal phthalamate and/or alkali metal phthalimidate with an alkali metal hypohalite, the first stage being carried out substantially adiabatically and both stages being carried out at high flow rates, wherein phthalimide and/or phthalamic acid is first dissolved in a certain amount of an alkali metal hydroxide solution, the resulting solution is mixed with a hypohalite and reacted at a particular temperature, acid is then added and the reaction is completed at a particular temperature. The compounds obtainable by the process of the invention are valuable starting materials for the preparation of dyes, crop protection agents and scents.

13 Claims, No Drawings

CONTINUOUS PREPARATION OF ISATOIC ANHYDRIDE

This is a continuation of application Ser. No. 108,580 filed Dec. 31, 1979, now abandoned.

The present invention relates to a process for the continuous preparation of isatoic anhydrides by two-stage reaction of an alkali metal phthalamate and/or alkali metal phthalimidate with an alkali metal hypohalite, the first stage being carried out substantially adiabatically and both stages being carried out at high flow rates, wherein phthalimide and/or phthalamic acid is first dissolved in a certain amount of an alkali metal hydroxide solution, the resulting solution is mixed with a hypohalite and reacted at a particular temperature, acid is then added and the reaction is completed at a particular temperature.

German Published Applications DAS Nos. 1,950,281 and 2,000,698 disclose a process for the continuous preparation of anthranilic acid by reacting an alkali metal phthalamate and/or alkali metal phthalimidate with a hypohalite in an aqueous medium, wherein (a) an aqueous solution of an alkali metal phthalamate and/or an alkali metal phthalimidate and an aqueous solution of an alkali metal hypochlorite are mixed in a mixing apparatus, (b) the resulting mixture is reacted in the first part of a narrow reaction tube at a high flow rate, at from 10° to 50° C. under substantially adiabatic conditions, thereafter (c) the reaction mixture issuing at a high flow rate from the first part of the reaction tube is finally reacted in the second part of the said tube at from 60° to 80° C. and (d) anthranilic acid and/or isatoic anhydride are isolated in a conventional manner from the alkaline reaction mixture which issues from the reaction tube.

In this process, only a part of the free alkali metal hydroxide solution is used when dissolving the starting material, and another part is added to the hypochlorite solution. It is advantageous to use aqueous solutions containing from 10 to 50 percent by weight of phthalimide and/or phthalamic acid, containing from 1 to 1.1 moles of alkali metal hydroxide per mole of phthalimide and/or phthalamic acid. The prior publications state that the aqueous hypohalite solution advantageously contains from 8 to 15 percent by weight of hypohalite and from 0 to 3, preferably from 0.02 to 2.1, moles of alkali metal hydroxide per mole of phthalimide and/or phthalamic acid. In Example 1 (relating to the preparation of anthranilic acid) alkali metal hydroxide is present both in the phthalimide solution, in an amount of 1.1 moles of NaOH per mole of phthalimide, and in the hypochlorite solution (1.4 moles of NaOH per mole of phthalimide).

German Published Application DAS No. 1,950,281 states that the formation of the end product is influenced by varying the alkali concentration in the starting solutions. If the starting mixture contains from 0.9 to 1.1 moles of alkali per mole of phthalimide and/or phthalamic acid, isatoic anhydride is obtained. It is only in this case that the DAS provides—as shown by Example 2—that all the alkali should be added to the starting material. Only in the case of the preparation of anthranilic acid, but not in the case of the preparation of isatoic anhydride, may a reducing agent be added during stage (b) and/or stage (c), as shown by German Published Application DAS No. 2,000,698 in contrast to German Published Application DAS 1,950,281. It is true that sulfurous acid is mentioned amongst the reducing agents used for the preparation of anthranilic acid, but, as is shown by the Example and by the description of German Published Application DAS 2,000,698, sodium sulfite and sodium bisulfite are preferred. Specific values of the residence time of the reaction before adding the reducing agent, and of the pH after addition of the latter, are not given. As is shown by German Published Applications DAS Nos. 2,000,698 and 1,950,281 (column 4, lines 56–60), the reaction mixture obtained at the end of the reaction is in the form of an alkaline solution. Only when working up the reaction mixture to obtain anthranilic acid is acid added in order to precipitate the end product. In the case of the preparation of isatoic anhydride (Example 2 of German Published Application DAS 1,950,281), a reducing agent is not added, and only after the end of the reaction, namely during working up, is the pH brought to 7 by adding acid and the precipitated end product isolated. The process gives isatoic anhydride in unsatisfactory yield, purity and space-time yield.

German Pat. No. 127,138 discloses that phthalimide, in alkaline solution, can be reacted with a hypohalite to give isatoic anhydride. The difficulties which occur in this reaction, in particular the unsatisfactory yield and unsatisfactory purity of the end product, are described by E. Mohr, J. pr. Chemie (2), 80 (1909), 1–33. Trouble-free operation of this process, particularly on an industrial scale, is not possible.

German Published Application DAS No. 1,287,580 describes the preparation of isatoic anhydrides by reacting phthalimide and a hypohalite. The phthalimide is employed in the form of an aqueous solution of its salt and the hypohalite is added before more than 50 percent of the phthalimide has hydrolyzed in solution. After addition of the halite solution, from 18,000 to 30,000 gram calories are liberated in the reaction solution, before the latter is brought to a pH of from 5.5 to 9. German Laid-Open Application DOS No. 1,770,458 discloses that good yields of isatoic anhydride can only be obtained if the phthalamate solutions employed contain not less than 5 percent of the alkali metal phthalimidate. As is shown by the description and the Examples, phthalamic acid solutions which are free from phthalimide require a large excess of alkali for their decomposition and this excess reduces the yield of end product, due to formation of anthranilic acid and anthranoyl-anthranilic acid. The presence of phthalimide or salts thereof however entails disadvantages. First, the phthalimide has to be prepared in a separate process step from phthalic anhydride; secondly, phthalimide is of limited stability in alkaline solution, since it easily hydrolyzes to a phthalamate.

German Laid-Open Application DOS No. 2,258,150 discloses a process for the preparation of unsubstituted or substituted isatoic anhydride by reacting an alkali metal salt of unsubstituted or substituted phthalamic acid with a hypohalite in an aqueous medium in the presence of bromine, iodine and/or a haloamide. It is true that sulfamic acid and its derivatives may be used as catalysts, but they are always added before the start of the reaction. All Examples show that the catalyst, for example sulfamic acid, is added before adding the hypohalite. The aqueous hypohalite solutions in general contain from 5 to 15, preferably from 12 to 14, percent by weight of hypochlorite and may additionally contain from 0.01 to 0.1 mole of alkali metal hydroxide per mole of hypohalite. The initial mixture of the two starting materials may contain a total of 0.01 to 0.2 mole of alkali metal hydroxide (not including the alkali metal contained in the hypochlorite and in the phthalamate starting material) per mole of phthalamate starting material. The DOS shows that the reaction mixture remains alkaline up to the end of the reaction and that it is only neutralized with an acid, eg. sulfuric acid, when working up the mixture in order to isolate the end product (page 7, 1st paragraph). The Examples show that the reaction time between the addition of the hypohalite and the addition of the acid is from about 4 to 30 seconds, whilst in the sole Example of a continuous reaction in a tubular reactor, the reaction time is given as 12 seconds. After the addition of acid, the pH (as shown in the Examples) is from 7 to 7.5.

German Laid-Open Application DOS No. 2,346,308 describes a method of preparing unsubstituted or substituted isatoic anhydride by reacting an alkali metal phthalamate with a hypohalite in the presence of a polymerization inhibitor. The other features of the process, in particular as regards addition of acid, alkalinity of the reaction mixture, and sequence of addition of the reactants, correspond to those described in German Laid-Open Application DOS No. 2,258,150 and mentioned above. The residence time between the addition of the hypohalite and the addition of the acid is from 10 to 180 seconds, according to the Examples.

All these processes are unsatisfactory in respect of the yield and purity of the end product, especially in continuous operation on an industrial scale.

We have found that unsubstituted or substituted isatoic anhydride may be prepared advantageously by reacting an alkali metal phthalamate and/or alkali metal phthalimidate with a hypohalite in an aqueous medium if
(a) an unsubstituted or substituted phthalimide and/or phthalamic acid is dissolved in an aqueous alkali metal hydroxide solution, using a ratio of from 1 to 1.1 moles of alkali metal hydroxide per mole of phthalimide and/or per mole of phthalamic acid,
(b) the resulting aqueous solution of alkali metal phthalamate and/or alkali metal phthalimidate is mixed with an aqueous solution of an alkali metal hypohalite in a mixing apparatus,
(c) the resulting mixture is reacted in the first part of a reaction tube, at a high flow rate, under substantially adiabatic conditions at from 5° to 50° C. for from 0.1 to 3.5 seconds, thereafter
(d) an acid is added to the reaction mixture issuing at a high flow rate from the first part of the reaction tube, and the reaction is completed in the second part of the said tube at a pH of from 5 to 8 and at from 10° to 60° C., and
(e) the end product is isolated from the issuing reaction mixture in a conventional manner.

Further, we have found that it is advantageous if the reaction is carried out in the presence of bromine, iodine and/or an amide of the formula

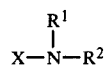

where $R^1$ is a sulfonic acid group, a sulfonate radical or a sulfonamide group, $R^2$ is hydrogen, an aliphatic radical, chlorine or bromine, X is chlorine, bromine or hydrogen, $R^1$ and $R^2$ may also, together with the adjacent nitrogen, be members of a heterocyclic radical which contains one or more sulfone groups, or phosphonyl groups of the formula

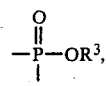

where $R^3$ is hydrogen or an alkali metal atom, the said groups being adjacent to the nitrogen, and $R^1$ and $R^2$ together may also be

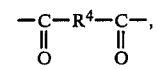

where $R^4$ is alkylene,

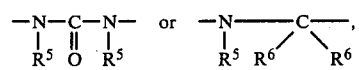

or
where $R^5$ is hydrogen, chlorine or bromine and $R^6$ is an aliphatic radical.

Where phthalimide, phthalamic acid, sodium hydroxide, hydrochloric acid and sodium hypochlorite are used, the reaction may be represented by the following equations:

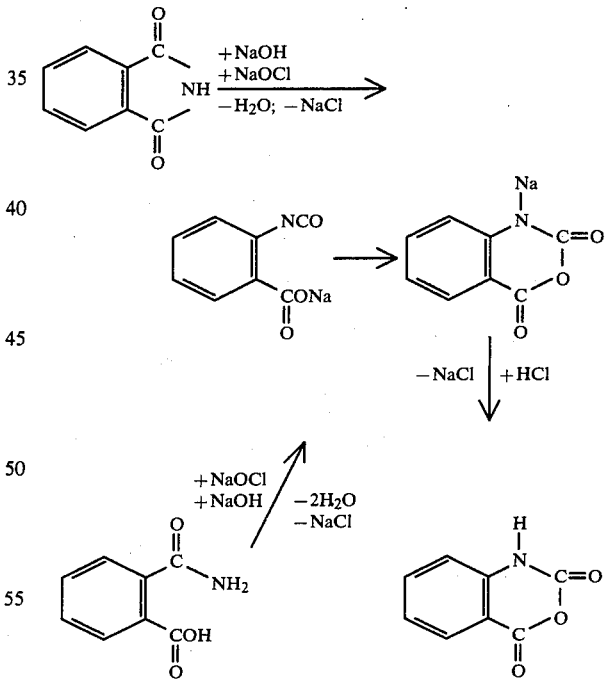

Compared to the conventional processes, the process according to the invention gives unsubstituted or substituted isatoic anhydride more simply and more economically, and in better yield, greater purity and better space-time yield. The reaction takes place more rapidly and can accordingly be carried out in substantially smaller tubular reactors. As a rule, the product leaving the tubular reactor is already in the form of a crystal sludge of isatoic anhydride, which can advantageously be collected in a receiver and worked up without any after-treatment. The end product is obtained in the form of coarser and better-developed crystals, of lower residual moisture content than the product obtained by the prior art processes. The crystals obtained are less smeary, can be filtered and dried more easily, and permit more rapid and more trouble-free transport of the solid in the downstream drying unit. Compared to the conventional process, addition of acid in a neutralizing bath is dispensed with; the reaction and neutralization take place more rapidly and pH fluctuations, which particularly in conventional stirred kettle neutralization lead to decomposition of the end product, are avoided. Hence, the process according to the invention is safer in operation and requires fewer operatives and supervisors. The total operating time, including the preparation of the aqueous starting mixture and the working up of the reaction mixture, is less in the case of the process according to the invention. All these advantageous results are surprising in view of the prior art. It was not to be expected, from the cited Patents, that good results would be achieved by the process of the invention, even though the reaction is also carried out with an alkali metal phthalamate alone, and without hydrolysis of the phthalimide according to the conditions claimed in German Published Application DAS No. 1,287,580. If phthalimide is used as the starting material, it is surprising, in view of the said DAS, that as a rule, and indeed preferably, the hypohalite is added in the novel process after more than 50 percent of the phthalimide has hydrolyzed in solution; advantageously, more than 95 percent of the phthalimide is hydrolyzed before adding the hypohalite. It would also have been expected from the very short reaction times of the process according to the invention that a heterogeneous mixture with a high proportion of unconverted starting material and of by-products would be formed. Since a prolonged reaction time results in perchlorinated by-products, which tend to decompose, sometimes explosively, the process according to the invention is safer in operation.

The starting materials used are unsubstituted or substituted phthalimides, phthalamic acids, alkali metal phthalamates (the phthalamate starting material) and alkali metal hypohalites, as a rule hypochlorites and hypobromites in the form of appropriate aqueous alkaline solutions.

Preferred isatoic anhydrides are those of the formula

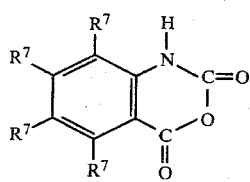

and accordingly preferred phthalamic acids are those of the formula

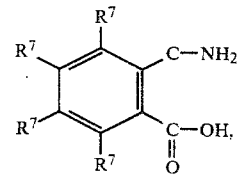

preferred phthalamate salts to use as starting materials, advantageously potassium salts and especially sodium salts, are salts of acids of the formula III, and preferred phthalimides are those of the formula

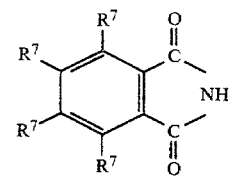

where the individual radicals $R^7$ may be identical or different and each is an aliphatic radical, preferably alkyl of 1 to 4 carbon atoms, hydrogen, halogen, preferably bromine or especially chlorine, carboxyl or a carboxylate group, especially an alkali metal carboxylate group, eg. a sodium carboxylate group or potassium carboxylate group. The preferred starting materials advantageously do not contain more than one carboxyl or alkali metal carboxylate group and not more than one halogen in addition to the carboxyl group and carbamido group required to form the anhydride ring.

Examples of suitable starting materials are the following phthalamic acids, as such or in the form of salts, and the corresponding phthalimides: orthophthalamic acid, 3-chlorophthalamic acid, 4-bromophthalamic acid, 3,5-dichlorophthalamic acid, 3,6-dichlorophthalamic acid, 3-carboxyphthalamic acid, 3-carboxy-6-chlorophthalamic acid, 3-methylphthalamic acid, 4-ethylphthalamic acid, 6-tert.-butylphthalamic acid, 4-sodium carboxylatophthalamic acid and 4-n-propyl-5-chlorophthalamic acid.

In stage (a), the starting material is dissolved in an aqueous alkali metal hydroxide solution, advantageously potassium hydroxide solution and especially sodium hydroxide solution. It is advantageous to use an aqueous solution which contains from 5 to 50, preferably from 15 to 30, percent by weight (based on the amount of water) of phthalimide and/or phthalamic acid and from 1 to 1.1, preferably from 1 to 1.02, mole of alkali metal hydroxide per mole of phthalimide and/or per mole of phthalamic acid. The solution is advantageously prepared continuously at from $-5°$ to $+50°$ C., preferably from 20° to 30° C., under atmospheric or superatmospheric pressure. If a catalyst, for example as described in German Laid-Open Application DOS No. 2,346,308 or advantageously as described in German Laid-Open Application DOS No. 2,258,150, is used, it is advantageously added to the starting material, or to its solution, as early as stage (a). However, it is also possible to add the catalyst, advantageously mixed with water, to the starting mixture, separately from or together with the hypohalite.

Advantageous catalysts are bromine, iodine and/or the above amides I, in general in an amount of from 0.0001 to 0.1, preferably from 0.001 to 0.01, mole of catalyst per mole of phthalimide or of phthalamic acid. Instead of the above catalysts, compounds which form the said compounds under the reaction conditions may be used, for example bromides and iodides in place of bromine or iodine. Advantageously, a water-soluble halide is used. These are preferably in the form of their alkaline earth metal salts and especially of their alkali metal salts, for example calcium bromide, calcium iodide, magnesium bromide, magnesium iodide, lithium bromide, lithium iodide and especially sodium bromide and iodide and potassium bromide and iodide. Preferred amides I are those where $R^1$ is a sulfonic acid group, a sulfonate radical, especially an alkali metal sulfonate radical, such as a sodium sulfonate or potassium sulfonate radical, or a sulfonamide group, $R^2$ is chlorine, bromine, alkyl of 1 to 4 carbon atoms or, in particular, hydrogen, X is bromine, chlorine or, advantageously, hydrogen, and $R^1$ and $R^2$ may also, together with the adjoining nitrogen, be members of a heterocyclic, 5-membered or 6-membered ring, which contains one or more sulfone groups, or phosphonyl groups of the formula

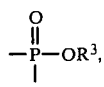

where $R^3$ is hydrogen or an alkali metal atom, especially a sodium atom or potassium atom, the said sulfone or phosphonyl groups being adjacent to the nitrogen, and $R^1$ and $R^2$ together may also be

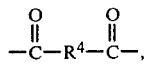

where $R^4$ is alkylene of 2 to 4 carbon atoms,

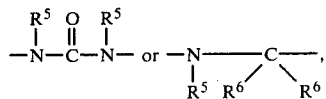

$R^5$ is hydrogen, chlorine or bromine and $R^6$ is alkyl of 1 to 4 carbon atoms, especially methyl. A phenylene nucleus may be fused to the above heterocyclic ring. Advantageously, the heterocyclic radical contains 2 sulfone or phosphonyl groups adjacent to the nitrogen or two or three sulfonamido or phosphonamido groups, especially in the same ring where polynuclear heterocyclic radicals are concerned. The above preferred radicals may in addition be substituted by groups or atoms which are inert under the reaction conditions, eg. chlorine, bromine or alkyl of 1 to 4 carbon atoms, or carboxyl or carboxylate groups present as substituents of the phenyl nucleus.

Examples of suitable catalysts are glutarimide, adipimide and succinimide and, preferably, cyanuric acid, 5,5-dimethylhydantoin, trisulfamide, N-methyl-sulfamic acid and sodium triimidometaphosphate, and appropriate mixtures of the above amides I. Sulfamic acid and its salts, advantageously alkali metal salts, such as the sodium salt or potassium salt, and in particular sulfamide, are especially preferred and may also be used as mixtures with the above amides I.

The aqueous hypohalite solutions, preferably hypochlorite solutions, used in stage (b) advantageously contain from 5 to 15, especially from 12 to 14, percent by weight of hypohalite, preferably hypochlorite, and no substantial amounts, namely at most up to 0.1 mole, and in particular up to 0.01 mole, of excess alkali metal hydroxide per mole of phthalimide and/or phthalamic acid. Preferred alkali metal hypochlorites are the potassium compound and more especially the sodium compound. In general, the reaction is carried out with from 1 to 2, preferably from 1 to 1.1, moles of hypohalite per mole of phthalimide and/or phthalamic acid. Advantageously, the starting material, in the form of the aqueous alkaline solution obtained from stage (a), and having the concentration stated earlier, is mixed, in stage (b), with the alkali metal hypohalite solution, preferably the alkali metal hypochlorite solution, in the above ratio, in a mixing apparatus. The latter may be a mixing cell, mixing nozzle or chamber fitted with a high-speed stirrer. Mixing is as a rule carried out continuously at from 0° to 50° C., advantageously from 25° to 45° C., under atmospheric or superatmospheric pressure.

The reaction is advantageously carried out in 2 reaction spaces (stages (c) and (d)), under conditions which substantially avoid back-mixing in both spaces, and substantially adiabatically in stage (c) and advantageously also in stage (d). In stage (c), the heat of reaction generated as a rule raises the reaction mixture to 20°–50° C. From the mixing apparatus, the reaction mixture passes into the reaction space of the first reaction stage (stage c), which consists of a reaction tube, which is advantageously narrow, and after having undergone reaction there the mixture passes into the reaction space of the next stage (stage d), which advantageously is a further narrow reaction tube; more especially, stages (c) and (d) are advantageously carried out in a single narrow reaction tube. The mixing apparatus, the reaction space in which the first stage is carried out, and the solutions of the starting materials, do not require cooling. The acid is introduced, advantageously through mixing nozzles, at the end of stage (c) and the beginning of stage (d). Preferably, in the process according to the invention, back-mixing in stage (c) is substantially avoided and the reaction mixture is rapidly removed from stage (c) and fed to stage (d), under conditions which substantially avoid back-mixing. Advantageously, the reaction mixture is given a high flow rate by employing a narrow cross-section of the reaction tube in both stages and by using appropriate conveying pumps. Examples of suitable pumps are jet pumps, rotary pumps, rotary piston pumps, Roots pumps, screw piston pumps, eccentric pumps, vane pumps, centrifugal pumps, axial-flow pumps and propeller pumps. In a preferred embodiment of the process, the flow rates are determined by the cross-section and length of the reaction tube. For example, it is advantageous to use reactor cross-sections of from 10 to 10,000 mm² and flow velocities of from 0.1 to 10, especially from 0.2 to 3, m/sec, preferably from 0.5 to 1 m/sec. At these flow rates, the starting material is as a rule substantially converted in stage (c) within a residence time of from 0.5 to 3.5, preferably from 1 to 2.7, seconds. The residence time in stage (c) is equal to the time required by the reaction mixture from addition of the hypohalite to addition of the acid. As a result of the high flow rate, the alkali metal salt formed is immediately withdrawn from the reaction space of stage (c), fed to the next stage, namely (d), and there reacted with acid, in general within a residence time of from 1 to 30, preferably from 2 to 20, seconds. The high flow rate at the same time substantially prevents back-mixing at all stages of the reaction of the mixture. In particular, back-mixing of the end product with the reaction mixture of stage (c) is avoided, and hence the formation of by-products by reaction of the hypohalite, or of the N-chlorinated phthalic acid monoamide, with the end product, and/or by corresponding reactions in the mixtures of stages (c) and (d) is suppressed. The reaction is carried out in stage (c) at from 5° to 50° C., preferably from 20° to 50° C., especially from 20° to 45° C., and in stage (d) at from 10° to 60° C., preferably from 30° to 45° C., in both stages under atmospheric or superatmospheric pressure. At the end of the reaction sequence, the reaction mixture is taken off and can be used as a suspension of isatoic anhydride, since the purity of the end product formed is excellent. The end product can alternatively be isolated from the acid solutions by subsequent filtration. For example, the reaction mixture can be fed to a stirred kettle and the crystal slurry formed therein can be subjected to suction filtration. If the product of the reaction is isatoic anhydride II in the form of its alkali metal salt, the latter is advantageously converted to the anhydride II by subsequent acidification.

In stage (d), the reaction mixture is treated with acid, advantageously an acid which is not reducing under the reaction conditions, and advantageously in an amount of from 1 to 1.2, especially from 1 to 1.1, equivalents per mole of starting material. Inorganic or organic acids may be used. Instead of monobasic acids, equivalent amounts of polybasic acids may be employed. Examples of suitable acids are hydrogen chloride, hydrogen bromide, perchloric acid, sulfuric acid, phosphoric acid, nitric acid, carbonic acid, sulfonic acids, eg. benzenesulfonic acid and p-toluenesulfonic acid, aliphatic carboxylic acids, eg. oxalic acid, formic acid, acetic acid, propionic acid, butyric acid and isobutyric acid, or mixtures of the above. The acids may be used in the concentrated form, as a mixture with one another and/or as a mixture with a solvent, especially water. Where aqueous acids are used, these are advantageously acids of from 1 to 100 percent strength by weight, for example hydrochloric acid of from 3 to 30 percent strength by weight or sulfuric acid of from 3 to 80 percent strength by weight. Preferred acids are hydrochloric acid, sulfuric acid and phosphoric acid. In stage (c), the reaction is as a rule carried out at a pH of from 14 to 8, preferably from 12 to 9, and in stage (d) at from 8 to 6, preferably from 7.5 to 6.4, especially from 7 to 6.3. The addition of acid is regulated so that in stage (d) a pH of the reaction mixture within the above pH range of from 5 to 8 results rapidly, preferably within from 0 to 0.1 second, after addition of the acid.

The compounds obtainable by the process of the invention are valuable starting materials for the preparation of dyes, crop protection agents and scents. The isatoic anhydrides may be converted to the corresponding anthranilic acids by hydrolysis with alkali. Regarding the use of the products, reference may be made to the cited Patents and to Ullmanns Encyklopädie der technischen Chemie, Volume 3, page 465 et seq. and Volume 13, page 499.

In the Examples which follow, parts are by weight and bear the same relation to parts by volume as that of the kilogram to the liter.

EXAMPLE 1

An apparatus comprising a mixing nozzle and a reaction tube 4 meters long and 76 millimeters in internal diameter is used. Per hour, 849 parts of liquid phthalimide are continuously dissolved, in a mixing nozzle, in 950 parts of aqueous 25 percent strength by weight sodium hydroxide solution and 7,900 parts of water and 20 parts/h of a 30 percent strength by weight aqueous solution of the sodium salt of sulfamic acid are continuously fed in. In the mixing nozzle, the solution formed is thereupon mixed with 3,100 parts per hour of an aqueous sodium hypochlorite solution (containing 421 parts of sodium hypochlorite; the latter in turn contains 13.6 percent by weight of active chlorine) at 25° C. The flow rate in the downstream reaction tube is 0.77 meter per second. At a distance of 2 meters from the mixing nozzle, the reaction tube has a second mixing nozzle, from which 800 parts per hour of 30 percent strength by weight hydrochloric acid are introduced into the reaction mixture. The residence time between the two mixing nozzles (stage c) is 2.6 seconds, whilst the residence time between the addition of the acid and the end of the reaction tube (stage d) is 2.4 seconds. In the first part of the reaction tube (stage c) the reaction mixture is reacted substantially adiabatically (at from 25° to 30° C.) and at pH 10, whilst in the remaining reaction space, namely stage (d), the reaction temperature is 35° C. and the pH is 6.8. The mixture is collected in a stirred kettle and is then filtered, and the filter residue is washed with water and dried. 922 parts per hour (98% of theory) of 99.8% pure isatoic anhydride, of melting point 235° C. (with decomposition), are obtained; the space-time yield is 102 parts per hour per liter.

COMPARATIVE EXAMPLE

If the reaction is carried out as described in Example 1, but, instead of introducing acid in the reactor, the reaction mixture is subsequently neutralized in a stirred kettle with 850 parts per hour of 30 percent strength by weight aqueous hydrochloric acid, the use, per hour, of 849 parts of phthalimide, 12,722 parts of water, 1,027 parts of 25 percent strength by weight sodium hydroxide solution, 5.5 parts of sulfamic acid, 3,130 parts of aqueous sodium hypochlorite solution (containing 425 parts of sodium hypochlorite; 13.6 percent by weight of active chlorine) results in 800 parts per hour (85% of theory) of 97–99% pure isatoic anhydride, of melting point 230° C. (with decomposition). Space-time yield: 14 parts per hour per liter.

EXAMPLES 2 AND 3

The starting materials listed in the Table are reacted by a method similar to Example 1, and under the same conditions, and in the same ratios, as in Example 1.

TABLE

| Example | Parts | Starting material | End product | Yield in % of theory | Melting point in °C. |
|---|---|---|---|---|---|
| 2 | 1,054 | 4-chloro-phthalimide | chloro-isatoic anhydride | 95 | 198–204 |
| 3 | 1,109 | 4-carboxy-phthalimide | carboxy-isatoic anhydride | 90 | sodium salt: melting point >300 (with decomposition) |

We claim:

1. A process for the continuous preparation of unsubstituted or substituted isatoic anhydride by reacting an alkali metal phthalamate and/or an alkali metal phthalimidate with a hypohalite in an aqueous medium, which comprises:

(a) dissolving an unsubstituted or substituted phthalimide and/or phthalamic acid in aqueous alkali metal hydroxide solution, using a ratio of from 1 to 1.1 moles of alkali metal hydroxide per mole of phthalimide and/or per mole of phthalamic acid, (b) mixing the resulting aqueous solution of alkali metal phthalamate and/or alkali metal phthalimidate with an aqueous solution of an alkali metal hypohalite in a mixing apparatus, (c) reacting the resulting mixture in the first part of a reaction tube, at a high flow rate, under substantially adiabatic conditions at from 5° to 50° C. for 0.1 to 3.5 seconds, in the presence of bromine, iodine and/or an amide of the formula

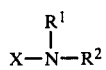   I where $R^1$ is a sulfonic acid group, a sulfonate radical or a sulfonamide group, $R^2$ is hydrogen, an aliphatic radical, chlorine or bromine, X is chlorine, bromine or hydrogen, $R^1$ and $R^2$ may also together with the adjacent nitrogen, be members of heterocyclic radical which contains one or more sulfone groups, or phosphonyl groups of the formula

where $R^3$ is hydrogen or an alkali metal atom, the said groups being adjacent to the nitrogen, and $R^1$ and $R^2$ together may also be

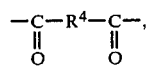

where $R^4$ is alkylene,

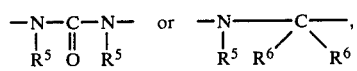

where $R^5$ is hydrogen, chlorine or bromine and $R^6$ is an aliphatic radical, (d) adding an acid to the reaction mixture issuing at a high flow rate from the first part of the reaction tube, and completing the reaction in the second part of said tube at a pH of from 5 to 8 and at from 10° to 60° C. and (e) isolating the end product from the issuing reaction mixture.

2. The process of claim 1, wherein the reaction is carried out with a phthalamic acid of the formula

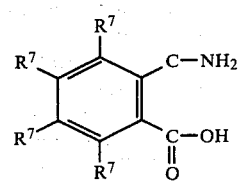   III or a salt of such an acid, or with a phthalimide of the formula

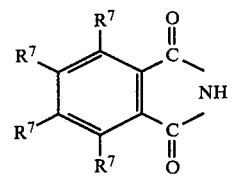   IV where the individual radicals $R^7$ may be identical or different and each is an aliphatic radical hydrogen.

3. The process of claim 1, wherein the reaction is carried out in the presence of glutarimide, adipimide, succinimide, cyanuric acid, 5,5-dimethylhydantoin, trisulfamide, N-methyl-sulfamic acid, sodium triimidometaphosphate, sulfamic acid, salts of sulfamic acid and/or sulfamide.

4. The process of claim 1, wherein the reaction is carried out with an aqueous hypohalite solution containing from 5 to 15 percent by weight of hypohalite.

5. The process of claim 1, wherein the reaction is carried out using a ratio of from 1 to 2 moles of hypohalite per mole of phthalimide and/or of phthalamic acid.

6. The process of claim 1, wherein the reaction is carried out with a flow rate of from 0.1 to 10 m/sec.

7. The process of claim 1, wherein the reaction is carried out with a residence time of from 1 to 30 seconds in stage (d).

8. The process of claim 1, wherein the reaction in stage (c) is carried out at from 20° to 50° C.

9. The process of claim 1, wherein the reaction in stage (d) is carried out at from 30° to 45° C.

10. The process of claim 1, wherein the reaction is carried out with from 1 to 1.2 equivalents of acid per mole of starting material.

11. The process of claim 1, wherein the reaction is carried out with hydrogen chloride, hydrogen bromide, perchloric acid, sulfuric acid, phosphoric acid, nitric acid, carbonic acid, benzenesulfonic acid, p-toluenesulfonic acid, oxalic acid, formic acid, acetic acid, propionic acid, butyric acid and/or isobutyric acid.

12. The process of claim 1, wherein the reaction in stage (c) is carried out at a pH of from 14 to 8.

13. The process of claim 1, wherein the reaction in stage (d) is carried out at a pH of from 8 to 6.

* * * * *